(12) United States Patent
Kang et al.

(10) Patent No.: US 11,587,048 B2
(45) Date of Patent: Feb. 21, 2023

(54) METHOD AND SYSTEM FOR MASSAGE APPARATUS-BASED USER INFORMATION TRANSACTION

(71) Applicant: BODYFRIEND CO., LTD., Seoul (KR)

(72) Inventors: Woong Chul Kang, Gyeonggi-do (KR); Soo Hyun Cho, Seoul (KR)

(73) Assignee: BODYFRIEND CO., LTD, Seoul (KR)

( * ) Notice: Subject to any disclaimer, the term of this patent is extended or adjusted under 35 U.S.C. 154(b) by 55 days.

(21) Appl. No.: 17/265,431

(22) PCT Filed: Nov. 30, 2018

(86) PCT No.: PCT/KR2018/015084
§ 371 (c)(1),
(2) Date: Feb. 2, 2021

(87) PCT Pub. No.: WO2020/032328
PCT Pub. Date: Feb. 13, 2020

(65) Prior Publication Data
US 2021/0357882 A1 Nov. 18, 2021

(30) Foreign Application Priority Data
Aug. 7, 2018 (KR) .................. 10-2018-0091622

(51) Int. Cl.
*G06Q 20/06* (2012.01)
*G06F 16/18* (2019.01)

(52) U.S. Cl.
CPC ....... *G06Q 20/065* (2013.01); *G06F 16/1805* (2019.01)

(58) Field of Classification Search
CPC .. G06Q 20/065; G06Q 20/06; G06F 16/1805; G06F 16/18
See application file for complete search history.

(56) References Cited

U.S. PATENT DOCUMENTS

| 2014/0195365 | A1* | 7/2014 | Krause | G06Q 30/08 |
| | | | | 705/26.3 |
| 2016/0342977 | A1* | 11/2016 | Lam | G06Q 20/0658 |
| 2017/0007126 | A1* | 1/2017 | Shahar | A61B 5/0002 |

FOREIGN PATENT DOCUMENTS

| JP | 2003-275263 A | 9/2003 |
| JP | 2003275263 A * | 9/2003 |

(Continued)

OTHER PUBLICATIONS

"Kaufman, Joanne, Where Fitness Nuts Go to Untangle Their Sore Muscles, Feb. 2, 25017, New York Times" (Year: 2017).*

*Primary Examiner* — Kenneth Bartley
*Assistant Examiner* — Gregory M James
(74) *Attorney, Agent, or Firm* — Bridgeway IP Law Group, PLLC; Sang Ho Lee; Hyun Woo Shin

(57) ABSTRACT

Provided are a method and a system for a massage apparatus-based user information transaction. According to one embodiment of the disclosure, a method for a massage apparatus-based user information transaction includes the steps of: inquiring whether a user gives prior-consent to provision of user information to the outside; if the user gives prior consent to the provision of user information to the outside, collecting, from the massage apparatus, user information including the user's biometric information, and storing same; providing the stored user information to a third party company server; calculating an amount of money to be paid to the user in accordance with the provision of the user information to the outside; and paying the calculated amount of money to the relevant user's account.

19 Claims, 5 Drawing Sheets

(56) References Cited

FOREIGN PATENT DOCUMENTS

| | | | |
|---|---|---|---|
| JP | 2017-059261 A | 3/2017 | |
| KR | 10-2014-0002409 A | 1/2014 | |
| KR | 10-2016-0117924 A | 10/2016 | |
| KR | 10-1729646 B1 | 4/2017 | |
| KR | 101729646 B1 * | 4/2017 | |
| KR | 10-2018-0010467 A | 1/2018 | |
| KR | 2018-0022324 A | 3/2018 | |
| KR | 10-2018-0052339 A | 5/2018 | |
| WO | WO-2016122183 A1 * | 8/2016 | ............. G06Q 30/06 |

* cited by examiner

METHOD AND SYSTEM FOR MASSAGE APPARATUS-BASED USER INFORMATION TRANSACTION

TECHNICAL FIELD

The present disclosure relates to a method and system for transacting user information on the basis of massage equipment and more particularly, to a massage equipment-based user information transaction method and system which enable users to be paid for providing their own biometric information acquired while using massage equipment to organizations and enable companies to increase sales in the end by motivating users to use products thereof.

BACKGROUND ART

While the importance of data as the core resources of the fourth industrial revolution is being highlighted, the problem of information protection that individuals who are information subjects are alienated has emerged.

For example, companies arbitrarily use personal information for marketing online or make gains even by selling personal information to other companies, but individuals do not benefit from their personal information at all.

However, in the coming era, individuals are being able to provide entire personal information including records of Internet transactions to organizations and get paid for the personal information.

In Japan, the "information bank," which is a data broker collecting and providing personal information to companies, was launched. In Europe, the idea of "data as labor," which requires that each individual receive compensation for data provided by himself or herself, is spreading.

While leading global information technology (IT) companies arouse controversy over personal data breaches, personal data sales to third parties, etc., the movement to see that the ownership of personal information belongs to individuals is becoming a new global trend.

The Japanese government proposed a bill which allows the use of personal information so that big data of customers may help companies to discover new businesses. The Japanese government decided to introduce the information bank which manages and administers data between individuals and companies.

About 1000 customers of the information bank select, write, and store information that can be provided to third parties, such as purchase histories, location information, and health information, through a smart phone application, and when the companies make public the types of data required by the companies, the purposes of use, etc., the information bank enables the customers to determine whether to provide their personal information. The information bank contracts with companies which require personal information for product development, market analysis, etc., such as travel agencies and health food companies, and then sells information that customers agreed to provide. The customers receive information charge or a promotion service in return for the information.

DISCLOSURE

Technical Problem

The present disclosure is directed to providing a massage equipment-based user information transaction method and system which enable users to be paid for providing their own biometric information acquired while using massage equipment to a third party organization and enable companies to increase sales in the end by motivating users to use products thereof.

Technical Solution

One aspect of the present disclosure provides a method of transacting user information on the basis of massage equipment, the method including inquiring of a user whether the user agrees to externally provide user information in advance, when the user agrees to the inquiry in advance, collecting user information including biometric user information from the massage equipment and storing the user information, providing the stored user information to a third party company server, calculating the amount of money to be paid to the user for externally providing the user information, and paying the calculated amount of money to an account of the user.

Another aspect of the present disclosure provides a system for transacting user information on the basis of massage equipment, the system including massage equipment configured to acquire biometric user information when the user agrees to an inquiry about whether a user agrees to externally provide user information in advance, a service providing server configured to collect user information by receiving the biometric user information from the massage equipment, provide the collected user information to a third party company server, calculate the amount of virtual currency to be paid to the user for externally providing the user information, and pay the calculated amount of virtual currency to a corresponding user account, and the third party company server configured to buy the collected user information through the service providing server.

Advantageous Effects

With the massage equipment-based user information transaction method and system configured as described above according to embodiments of the present disclosure, a user can immediately acquire his or her own biometric information while using massage equipment and can be rewarded for externally providing his or her own acquired biometric information.

Also, when rewarding a user for selling user information, a company differentially calculates the amount of money to be paid according to details of using a variety of products thereof including the frequency of using massage equipment. Accordingly, it is possible to increase sales in the end by motivating the user to consume products of the company.

Further, when blockchain-based dedicated virtual currency is used in buying and selling transactions among a massage equipment user, a service company, and a third party company, it is possible to track a transfer path of user information and detailed usage information of the user information, and it is impossible to forge details of buying and selling transactions. Accordingly, a reliable transaction system can be implemented.

DESCRIPTION OF DRAWINGS

Various aspects will be described with reference to the drawings, and like reference numerals are used to collectively designate like elements. In the following embodiments, a plurality of specific details will be suggested for comprehensive understanding of one or more aspects of the purpose of description. However, it will be apparent that the aspect(s) will be embodied without having the specific details. In other examples, known structures and devices will be illustrated as a block diagram to easily describe one or more aspects.

BEST MODE OF THE INVENTION

Figure 1:
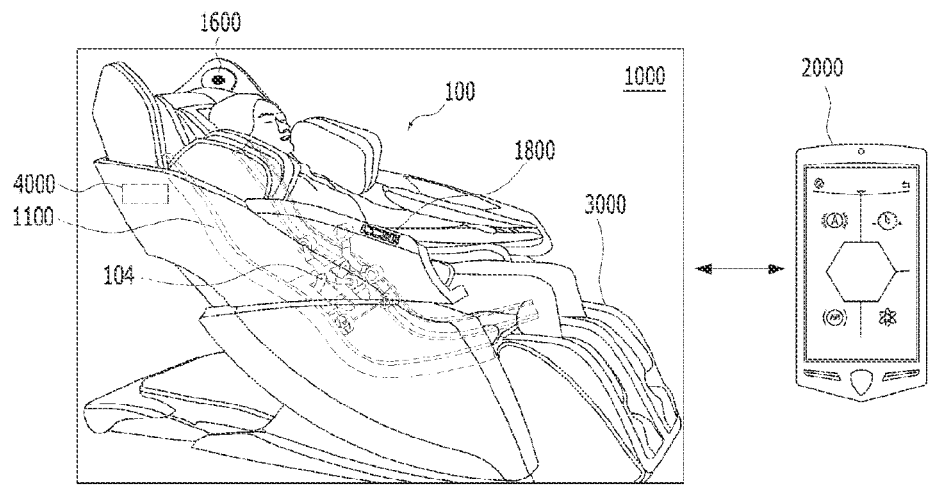
FIG. 1 is a diagram schematically showing a massage equipment 1000 according to an embodiment of the present disclosure.

A method of transacting user information on the basis of massage equipment includes inquiring of a user whether the user agrees to externally provide user information in advance, when the user agrees to the inquiry in advance, collecting user information including biometric user information from the massage equipment and storing the user information, providing the stored user information to a third party company server, calculating the amount of money to be paid to the user for externally providing the user information, and paying the calculated amount of money to an account of the user.

MODES OF THE INVENTION

The objects, features, and advantages of the present disclosure will become more apparent through the accompanying drawings and the following embodiments. The following specific structural or functional descriptions are exemplary to merely describe the embodiments of the present disclosure. The embodiments of the present disclosure can be implemented in various forms and should not be construed as being limited to the embodiments described in the present specification or application.

Since various modifications can be made and diverse embodiments are applicable to the embodiments according to the concept of the present disclosure, specific embodiments will be illustrated in the drawings and described in detail. However, these specific embodiments should not be construed as limiting the embodiments according to the concept of the present disclosure but should be construed as extending to all modifications, equivalents, and substitutes within the spirit and technical scope of the present disclosure.

Terms, such as first and/or second, may be used to describe various elements, but the elements are not limited by these terms. The terms are used merely for the purpose of distinguishing one element from other elements. For example, a first element may be named a second element and, similarly, a second element may be named a first element without departing from the scope according to the concept of the present disclosure.

It will be understood that when an element is referred to as being "connected" or "coupled" to another element, it may be directly connected or coupled to the other element, or an intervening element may exist. In contrast, it will be understood that when an element is referred to as being "directly connected" or "directly coupled" to another element, there is no intervening element. Other expressions describing the relationships between elements, that is, "between" and "immediately between" or "neighboring" and "immediately neighboring," should be interpreted in the same manner.

The terms used in the present specification are used to describe only specific embodiments and are not intended to limit the present disclosure. Singular forms are intended to include plural forms unless the context clearly indicates otherwise. It will be further understood that the terms "include," "have," or the like used herein specify the presence of stated features, numerals, steps, operations, elements, parts, or a combination thereof but do not preclude the probability of presence or addition of one or more other features, numerals, steps, operations, elements, parts, or combinations thereof.

Unless otherwise defined, all terms used herein, including technical or scientific terms, have the same meanings as terms generally understood by those of ordinary skill in the art to which the present disclosure pertains. Terms defined in a generally used dictionary are to be interpreted to have meanings consistent with the contexture meanings in the relevant field of art and are not interpreted to have ideal or excessively formal meanings unless clearly defined herein.

According to an embodiment of the present disclosure, "massage equipment" may refer to massage equipment including a body massage unit and a leg massage unit.

Hereinafter, embodiments of the present disclosure will be described in detail with reference to the accompanying drawings.

FIG. 1 is a diagram schematically showing a massage equipment 1000 according to an embodiment of the present disclosure.

The massage equipment 1000 according to the embodiment of the present disclosure may have an area for accommodating at least a part of a user's body and include a body massage unit 100 for massaging the user's body and a leg massage unit 3000 for massaging the user's legs.

The body massage unit 100 may give a massage to at least a part of the user's body. The body massage unit 100 may include a massage module 1700 for providing a massage function to at least a part of the user's body, an audio output module 1600 for providing an audio output to the user in an arbitrary form, a main frame 1100 constituting a frame of the body massage unit 100, and a user input unit 1800 for receiving an input from the user in an arbitrary form.

The elements included in the body massage unit 100 merely correspond to an exemplary embodiment, and the body massage unit 100 may include various elements other than those mentioned above.

Also, the shape and structure of the massage equipment 1000 shown in FIG. 1 are exemplary, and various forms of massage equipment 1000 may also fall within the scope of the present disclosure as long as not departing from the scope of rights defined in the claims of the present disclosure.

The body massage unit 100 may have an arbitrary form of space for accommodating the user. The body massage unit 100 may have a form of space corresponding to the shape of the user's body. For example, as shown in FIG. 1, the body massage unit 100 may be implemented in a seat type which may accommodate the whole or a part of the user's body.

A part of the body massage unit 100 which comes in contact with the ground may include an arbitrary material for increasing friction or an arbitrary member for increasing friction (e.g., an anti-slip pad) and wheels for enhancing mobility of the massage equipment 1000.

At least a part of the body massage unit 100 may slide. For example, when the body massage unit 100 starts a massage, at least a part of the body massage unit 100 may slide forward. Also, the body massage unit 100 may be tilted backward. As a result, the body massage unit 100 may provide the massage while tilted backward.

According to the embodiment of the present disclosure, the massage equipment 1000 may include at least one air cell (not shown). The air cell may be placed at a user's shoulder part, a pelvis part, an arm massage unit, the leg massage unit 3000, and the like. However, the placement of the air cell is not limited thereto, and the air cell may be disposed at various parts of the massage equipment 1000.

The massage equipment 1000 may include an air supply unit, and the air supply unit may inflate the air cell by supplying air to the air cell. The air supply unit may be placed in the body massage unit 100 and the leg massage unit 3000. Also, the air supply unit may be placed outside the massage equipment 1000.

The leg massage unit 3000 may provide a leg massage to the user.

For example, the leg massage unit 3000 may include a calf massage unit for massaging the user's calves and/or a foot massage unit for massaging the user's feet.

The leg massage unit 3000 can be adjusted in length according to the user's physical features. For example, when a tall user uses the massage equipment 1000, the leg massage unit 3000 needs to be lengthened because the user's calves are long. Also, when a short user uses the massage equipment 1000, the leg massage unit 3000 needs to be shortened because the user's calves are short. Accordingly, the leg massage unit 3000 may provide a leg massage customized for the user's height.

The massage module 1700 may be provided in the body massage unit 100 to provide an arbitrary form of mechanical stimulus to the user accommodated in the body massage unit 100. As shown in FIG. 1, the massage module 1700 may move along the main frame 1100 provided in the body massage unit 100.

For example, a rack gear may be provided on the main frame 1100 of the body massage unit 100, and the massage module 1700 may provide a mechanical stimulus to various parts of the user's body while moving along the rack gear. The massage module 1700 may include a ball massage unit or a roller massage unit but is not limited thereto.

The main frame 1100 constitutes the internal frame of the body massage unit 100 and may be formed of a metal material or a plastic material. For example, the main frame 1100 may be formed of iron, an alloy, steel, or the like. However, the material of the main frame 1100 is not limited thereto, and the main frame 1100 may be formed of various rigid materials.

According to the embodiment of the present disclosure, the massage equipment 1000 may include the audio output module 1600. The audio output module 1600 may be provided at various positions. For example, the audio output module 1600 may include a plurality of output units, such as an upper audio output unit disposed in an upper part of a seat unit which comes in contact with the user, forward audio output units attached to front parts of left and right arm massage units of the seat unit, and/or rear audio output units attached to rear parts of the arm massage units, but is not limited thereto. In this case, the audio output module 1600 may provide stereophonic sound, such as 5.1 channels, but is not limited thereto.

According to the embodiment of the present disclosure, the user may control the massage equipment 1000 using a massage equipment control device 2000. The massage equipment control device 2000 may be connected to the massage equipment 1000 through wired communication and/or wireless communication.

Figure 2A:
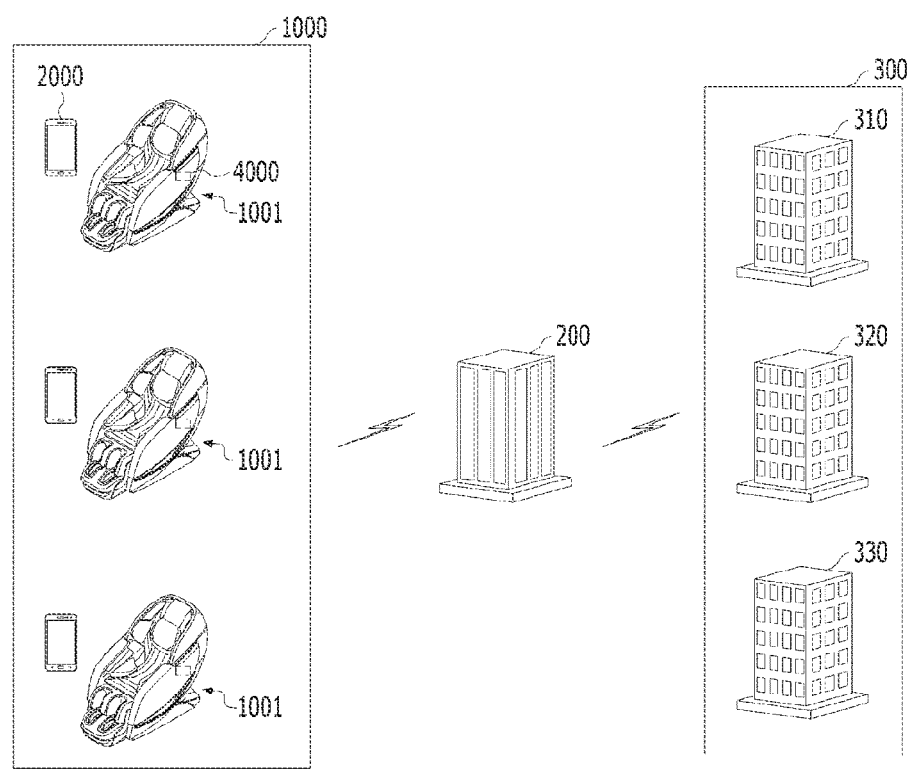
FIG. 2A is a diagram showing a schematic configuration of a system for transacting user information on the basis of massage equipment according to an embodiment of the present disclosure.
Figure 2B:
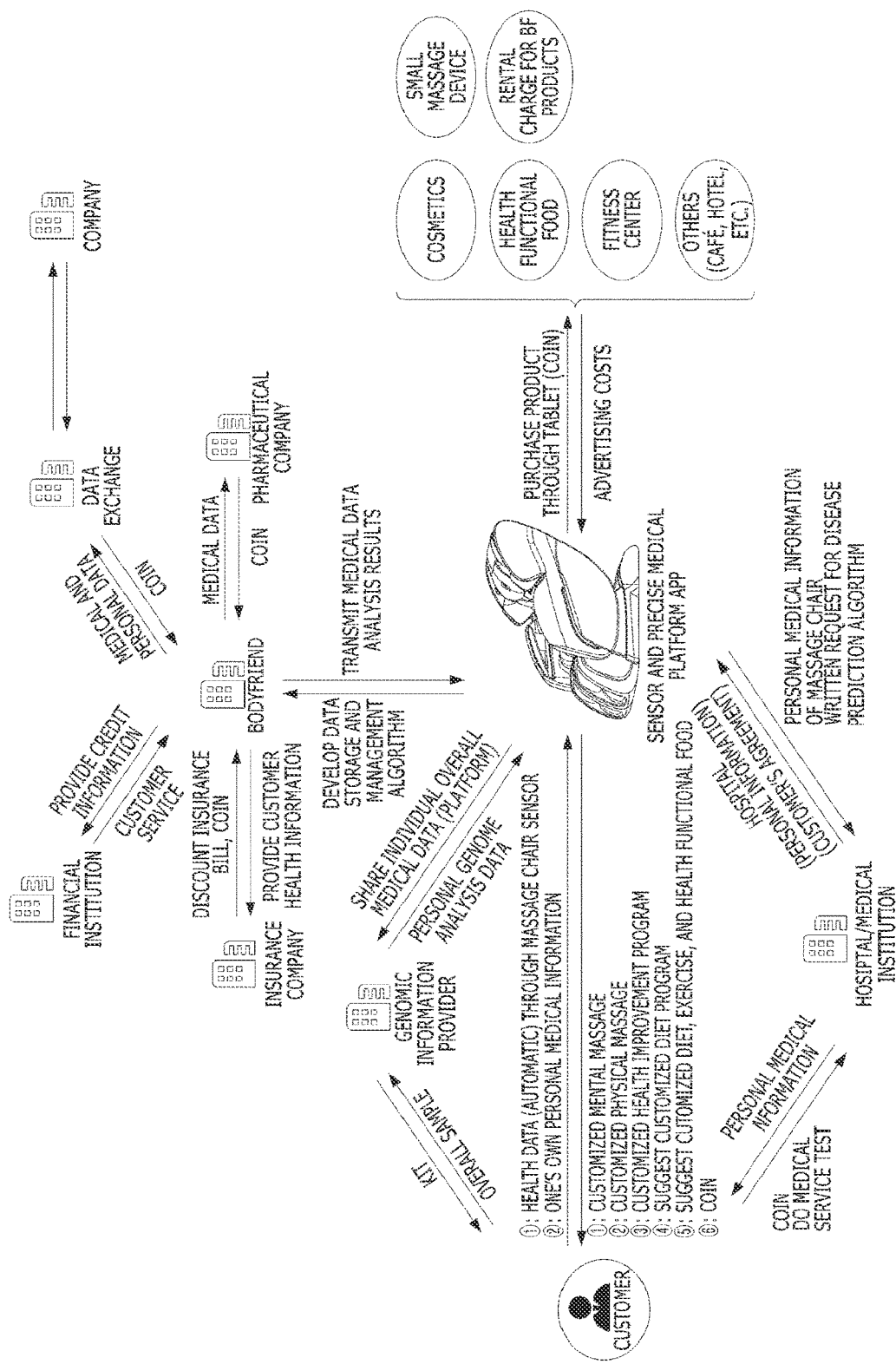
FIG. 2B shows a specific example of the system for transacting user information on the basis of massage equipment according to an embodiment of the present disclosure.

FIG. 2A is a diagram showing a schematic configuration of a system for transacting user information on the basis of massage equipment according to an embodiment of the present disclosure, and FIG. 2B shows a specific example of the system for transacting user information on the basis of massage equipment according to an embodiment of the present disclosure.

Referring to FIG. 2A, the system for transacting user information on the basis of massage equipment according to the embodiment of the present disclosure may include the massage equipment 1000, a service providing server 200 of a service providing company, and a third party company server 300 of a third party company.

The massage equipment 1000 may include at least one biometric information measurement module 4000. The biometric information measurement module 4000 may be installed in the massage equipment 1000 or provided outside the massage equipment 1000 and may be connected to the massage equipment control device 2000 through wired or wireless communication. Also, the biometric information measurement module 4000 may be installed in the massage equipment control device 2000 and is not limited to this case.

The massage equipment control device 2000 may include various electronic devices which are connected to the massage equipment 1000 through wired or wireless communication.

For example, the massage equipment control device 2000 may include a smart device, which is dedicated to the massage equipment 1000 and interoperates with the massage equipment 1000, and an internal module included in the massage equipment 1000. Also, the massage equipment control device 2000 may include a mobile smart device of a user. In the embodiment of the present disclosure, the mobile smart device is mentioned as an example of the smart device included in the massage equipment control device 2000, but the smart device is not limited thereto. The massage equipment control device 2000 may include a device capable of communicating information such as a laptop computer, a tablet personal computer (PC), a personal digital assistant (PDA), a smart television (TV), and a portable multimedia player (PMP).

Biometric information measured by the biometric information measurement module 4000 may be transmitted to the massage equipment 1000 and/or the massage equipment control device 2000.

The biometric information measurement module 4000 may include at least one of a sphygmomanometer, a blood glucose meter, a hematology analyzer, an electrocardiograph recorder, an electroencephalogram device, a body-composition measurement device, an electronic stethoscope, a peak flow meter, a momentum meter, a weighing machine, a body fat analyzer, medical image equipment, and a urinalysis machine. The biometric information measurement module 4000 may acquire biometric user information through automatic sensing.

According to an additional embodiment of the present disclosure, the massage equipment 1000 (and/or the server 200) may acquire biometric user information through another device. For example, the massage equipment 1000 (and/or the server 200) may acquire life-log data through a smart band.

Also, a massage equipment 1000 (and/or the server 200) may acquire personal medical information from hospitals and/or medical institutions under the consent of users. For example, the massage equipment 1000 (and/or the server 200) may acquire medication information, checkup information, medical examination information, electronic medical records, etc. of users from hospitals and/or medical institutions. However, types of information are not limited thereto, and the massage equipment 1000 (and/or the server 200) may acquire various types of information.

Further, the massage equipment 1000 (and/or the server 200) may acquire information related to lifestyle medicine. For example, the massage equipment 1000 and/or the server 200 may acquire information, such as an amount of exercise, intakes, drinking, smoking, defecation, and sleep, when the user directly inputs the information to an application installed on the user's device.

The massage equipment 1000 (and/or the server 200) may acquire personal genome analysis data from genomic information providers. For example, a user may take a genetic test through a genomic information provider, and the massage equipment 1000 (and/or the server 200) may receive results of the genetic test under the consent of the user.

The massage equipment 1000 may generate a specific algorithm by processing at least one piece of the acquired information mentioned above. For example, the massage equipment 1000 may generate algorithms such as an early myocardial infarction and heart attack diagnosis algorithm, an early cerebral infarction diagnosis algorithm, an early dementia diagnosis algorithm, an early obesity diagnosis algorithm, and diagnosis and prevention algorithms for various types of other diseases.

In this case, the massage equipment 1000 may generate a specific algorithm together with the service provider server 200. For example, the massage equipment 1000 may transmit the acquired information to the service provider server 200, and the service provider server 200 may generate a specific algorithm using the received information.

When the specific algorithm is generated, the massage equipment 1000 may analyze the acquired information through the specific algorithm and provide the analysis results to the user. For example, the massage equipment 1000 may determine a risk of dementia in the user using biometric information and/or medical information of the user and notify the user that he or she is at a high risk of dementia when the risk of dementia is high.

The massage equipment 1000 according to the embodiment of the present disclosure may constantly acquire biometric information every day and acquires genomic information which affects biometric values, medical record information, life-log data, and information related to lifestyle medicine together with the simple biometric information. Accordingly, accuracy in early diagnosis based on the algorithm may be increased.

Specifically, the massage equipment 1000 may analyze at least one of daily measured electrocardiogram values, daily measured blood cholesterol values, daily measured blood pressure values, the number of times, intensity, and duration of exercise during a predetermined time period, the number of drinking times and the volume of drink during a predetermined time period, sleeping hours, the number of smoking times, and the amount of smoking and calculate symptomatic information of various diseases, such as a probability of the user developing a cardiovascular disease in the future, and development prediction information of a corresponding symptom.

To this end, the massage equipment 1000 may access a statistical information database which stores various types biometric information, life-log data, information related to lifestyle medicine, user genome information, statistical information experientially or numerically calculated from medical treatment information, electronic medical records, and a time period from when a symptom of a disease related to physical information appears to when the disease develops, and disease-specific symptomatic information related to types and symptoms of various diseases.

Also, the massage equipment 1000 according to the embodiment of the present disclosure may provide a customized massage according to the user information acquired in the above-described manner. The customized massage may include a blood pressure control massage, a dementia prevention massage, a depression prevention massage, and a massage for preventing a specific disorder.

The massage equipment control device 2000 may inquire whether the user agrees to externally provide the user information in advance. For example, the massage equipment control device 2000 may inquire whether the user agrees in advance through an execution screen of a display or voice from a speaker and receive an answer to the inquiry from the user.

When the user inputs advance consent to externally provide user information, the massage equipment control device 2000 may further provide a screen for selecting a predetermined item that will be agreed to externally provide in advance from among one or more biometric user information items according to the user's request.

Alternatively, the massage equipment control device 2000 may provide an execution screen for selecting at least one biometric user information item from the beginning and also provide an execution screen which has been set to agree in advance to externally provide only biometric user information corresponding to the selected item.

For example, the user may selectively check only items corresponding to physical information that he or she wants to provide regarding at least one biometric information item among blood pressure, blood glucose, blood test, electronic stethoscope examination, expiratory flow, the amount of exercise, weight, body fat, medical image, and frequent urination.

Here, the massage equipment control device 2000 may selectively turn on or off a biometric information measurement module corresponding to the item selected by the user. For example, the massage equipment control device 2000 may automatically turn on only the biometric information measurement module corresponding to the item selected by the user to acquire a biometric measurement signal of the user and may automatically turn off the biometric information measurement module when the acquired biometric measurement signal is stored in the massage equipment control device 2000. In this way, it is unnecessary to turn on the power of all biometric information measurement modules provided in the massage equipment, and it is possible to efficiently manage power consumed by the massage equipment by turning on a necessary biometric information measurement module only.

Alternatively, the massage equipment control device 2000 may only collect a biometric measurement signal corresponding to an item that has been agreed in advance by the user among biometric measurement signals acquired from a plurality of biometric information measurement modules.

When there is an item that has been agreed in advance by the user to externally provide user information, the massage equipment control device 2000 may perform user authentication. For example, the massage equipment control device 2000 may provide a user authentication processing screen. When the user inputs an identification (ID) and a password to the user authentication processing screen, the service providing server 200 may perform user authentication by checking whether the input ID and password coincide with an ID and password previously stored in a database.

After the user authentication succeeds, the massage equipment control device 2000 maps a unique identifier of the authenticated user to a biometric measurement signal acquired from the biometric information measurement module 4000 and store the result as user information. Here, the user information may mean information obtained by mapping the user's individual identification information to the biometric measurement signal (hereinafter, a biometric measurement signal and biometric information may be interchangeably used).

The massage equipment control device 2000 maps the biometric user information to the user identification information and stores the result. This is a necessary process to pay the user for providing the user information and may also be a process required for the purpose of recognizing a change in the biometric measurement signal of the user over time and the like.

At a time point at which user information is sold to the third party company server 300 by the service providing server 200, personal identity information, unique identification information, etc. may be excluded from the user information or encrypted, which will be described below. In other words, the user information may be provided so that only information related to biometric measurement signals required by the third party company may be provided, and the security of sensitive personal information may be maintained.

The massage equipment control device 2000 may execute a dedicated application for performing the above-described functions. For example, the dedicated application may be downloaded from the service providing server 200 to the massage equipment control device 2000 through a network and installed.

Alternatively, when the massage equipment control device 2000 is a dedicated smart device of the massage equipment 1000 or a built-in module included in the massage equipment 1000, the dedicated application may be installed on the massage equipment control device 2000 by default during product manufacturing or production.

Each of a plurality of massage equipment 1000 may transmit user information acquired from each user to the service providing server 200. Also, one massage equipment 1000 may transmit pieces of user information separately acquired from a plurality of users to the service providing server 2000.

The service providing server 200 may collect user information received from the massage equipment 1000, perform a selling transaction of the collected user information with the third party company server 300, calculate the amount of money to be paid to the user for externally providing the user information, and pay the calculated amount of money to an account of the user. Here, the third party company may be at least one of a medical institution, an insurance company, a pharmaceutical company, a health food company, and a data exchange. The third party company may use information on the user, which is constant, connective, and integrated information acquired through the service providing server 200, in various businesses. For example, the third party company may use a plurality of pieces of user information in businesses such as generating health functional food, planning a customized exercise, proposing a customized diet, generating a diet program, and generating a program for preventing a specific disease.

According to another embodiment of the present disclosure, the massage equipment 1000 may induce the user to purchase a product through the massage equipment control device 2000. In this case, the product may include cosmetics, health functional food, fitness center vouchers, café vouchers, hotel vouchers, small massage devices, etc. but is not limited thereto.

For example, an interface for purchasing cosmetics, health functional food, etc. may be displayed on the massage equipment control device 2000. In this case, the displayed interface may be determined on the basis of user information (e.g., biometric information, medical information, and genomic information) acquired by the massage equipment 1000.

Specifically, products (e.g., types of proposed cosmetics, types of proposed health functional food, and a proposed small massage device) provided by the interface may be determined on the basis of the user information (e.g., biometric information, medical information, and genomic information) acquired by the massage equipment 1000.

Each element of the service providing server 200 will be described in detail below with reference to a role thereof.

Figure 3:
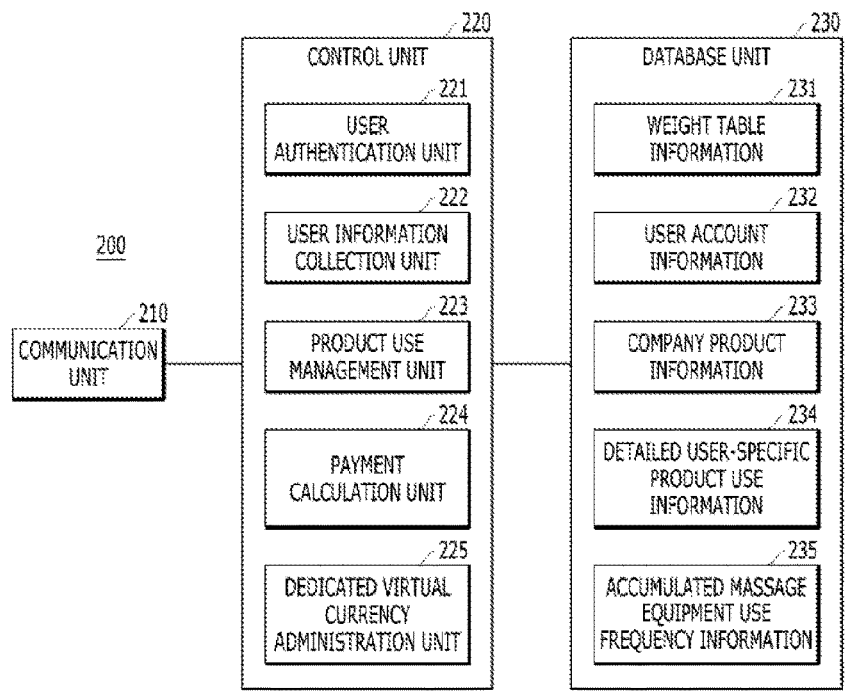
FIG. 3 is a diagram showing a schematic configuration of a service providing server according to an embodiment of the present disclosure.

FIG. 3 is a diagram showing a schematic configuration of a service providing server according to the embodiment of the present disclosure.

The service providing server 200 may include a communication unit 210, a control unit 220, and a database unit 230, and other elements may be added as necessary.

The communication unit 210 provides a channel for data transmission and reception in communication between the massage equipment control device 2000 and third party company servers 300. The communication unit 210 may use at least one of a wired network, an Internet protocol (IP) network which provide a service through the IP, a wireless broadband (Wibro) network, a third generation mobile network including a wideband code division multiple access (WCDMA) network, 3.5$^{th}$ generation mobile networks including a high speed downlink packet access (HSDPA) network and an long term evolution (LTE) network, a fourth generation mobile network including an LTE advanced network, a satellite network, and a wireless local area network (WLAN) including a Wi-Fi network.

The control unit 220 may control a plurality of hardware and software elements connected thereto and process or compute various types of data including multimedia data.

The control unit 220 may provide an application dedicated to massage equipment-based user information transaction to the massage equipment control device 2000 and update the database unit 230 with various types of information generated during execution of the dedicated application. Alternatively, the control unit 220 may update the database unit 230 with information input from the massage equipment control device 2000 through a company homepage.

The database unit 230 may store weight table information 231, user account information 232, company product information 233, detailed user-specific product use information 234, and accumulated user-specific massage equipment use frequency information 235 and may also store other information required for massage equipment-based user information transaction.

The control unit 220 may include a user authentication unit 221, a user information collection unit 222, a product use management unit 223, and a dedicated virtual currency administration unit 224.

The user authentication unit 221 may perform authentication of, for example, a user who tries to transact user information through the dedicated application or a user who tries to transact user information through a company homepage.

The user information collection unit 222 may map a unique identifier of the authenticated user to a biometric measurement signal acquired from the biometric information measurement module 4000 and collect the result as user information. A method of collecting the user information has been described above with reference to FIGS. 1 to 2B, and detailed description thereof will be omitted.

The product use management unit 223 may manage a consumption history of the user purchasing or renting a product of a company which sells the massage equipment 1000 and user-specific product use information of current situation of using products and the like.

Here, detailed usage information of the corresponding user may include at least one of a type of purchase indicating whether the user has rented or purchased a product of the service providing company, the type of a purchased product, the number of times of purchase, the number of purchased products, the amount of paid money, a rental period, a time period remaining until the rental end date, a current situation of uploading advertisement data of the product, and a current situation of purchase caused by recommendations to acquaintances. Such detailed usage information of the user may be stored in the database unit 230.

A payment calculation unit 224 may calculate the amount of money to be paid to the user for user information sold to a third party company by the service providing company.

Specifically, when calculating the amount of money to be paid to the user, the payment calculation unit 224 may differentially calculate the amount of money according to user information items that have been agreed in advance to externally provide and the user's frequency of using the massage equipment and pay the user the amount of money.

To this end, first, the user information collection unit 224 may acquire at least one of the number of user information items that have been agreed in advance to externally provide and types of the items. Also, the user information collection unit 224 may acquire the user's frequency of using the massage equipment 1000. Here, the user's frequency of using the massage equipment 1000 may be the number of times of use during a preset certain time period. The number of user information items that have been agreed in advance to externally provide, types of the items, and the user's frequency of using the massage equipment 1000 may be acquired from the database unit 230.

The payment calculation unit 224 may calculate the amount of money to be paid to the user in consideration of at least one of the number of user information items that have been agreed in advance to externally provide, types of the items, and the user's frequency of using the massage equipment 1000.

For example, when the user selects the items of blood pressure, weight, and body fat as user information, it is possible to calculate a part of the amount of money to be paid to the user by applying a weight which is differentially set according to the importance of each item and the number of selected items. Also, it is possible to calculate a part of the amount of money to be paid to the user by applying a weight which is differentially set according to the user's frequency of using the massage equipment 1000 during a preset time period. The total amount of money to be paid to the user may be calculated in consideration of the amount of money calculated as described above.

Also, the payment calculation unit 224 may calculate the amount of money as a compensation for a user who has used the massage equipment 1000 for a predetermined time or more and a predetermined number of times or more during a predetermined time period.

In addition, the payment calculation unit 224 may additionally pay for a specific event, which may be, for example, a case in which a user with a specific disease constantly provides user information in time series or a case in which a user acquires and provides genomic information and the like from a medical institution or a corresponding expert organization.

In the case of calculating the amount of money to be paid, the frequency of using the massage equipment 1000 is taken into consideration to motivate the user to continuously use the massage equipment 1000 so that the user may fully use the performance of the massage equipment 1000 and obtain positive massage effects on his or her body.

Meanwhile, when calculating the amount of money to be paid to the user, the payment calculation unit 224 may differentially calculate the amount of money according to at least one of the user information items that have been agreed in advance to externally provide, the user's frequency of using the massage equipment and pay the user the amount of money, and the user's detailed usage information related to various types of products of the company. Specific embodiments of calculating the amount of money to be paid to the user on the basis of such information will be described.

As an embodiment, the payment calculation unit 224 may differentially calculate the amount of money to be paid to the user according to at least one of user information items that have been agreed in advance to externally provide, the user's frequency of using the massage equipment, and a current situation of uploading advertisement data of at least one product of the service providing company.

To this end, the payment calculation unit 224 may calculate the number of times that the user has uploaded advertising content of at least one product of the service providing company online. Here, information on the number of times of uploading advertising content may be updated in real time in the database unit 230 through the dedicated application.

Also, the payment calculation unit 224 may acquire priority order information preset by the service providing company for the product of which the advertising content has been uploaded. Subsequently, the payment calculation unit 224 may calculate the amount of money to be paid in consideration of the number of times of uploading the advertising content and the acquired priority order information.

For example, the service providing company is a company related to healthcare products and sells massage equipment, water purifiers, air purifiers, mattresses or provides a rental service thereof. Among the products, the service providing company focuses on massage equipment as a representative product, and thus the highest order of importance may be given to the massage equipment among the products. Also, the service providing company may separately determine orders of importance for several types of massage equipment according to the functions, unit prices, etc. thereof. Information on the set order of importance may be stored in the database unit 230 and updated by the service providing server 200. Information on the number of times of uploading advertising content may be stored in the database unit 230 as the number of times that the advertising content has been uploaded to social network services and sites (SNSs) during a predetermined time period and may be updated by the service providing server 200.

The payment calculation unit 224 may increase the calculated amount of money when the user purchases a type of massage equipment with a higher order of importance among types of massage equipment and shares advertising content through SNSs a greater number of times during a predetermined time period. To this end, it is possible to use a weight table of weights which are differentially set according to the order of importance of products, weights which are differentially set according to the number of times of uploading advertising content during a predetermined time period, etc., and the weight table may be updated by the service providing server 200.

Here, the final amount of money calculated by the payment calculation unit 224 may be calculated in consideration of the number and types of user information items that have been agreed in advance to externally provide, the user's frequency of using the massage equipment, and a current situation of uploading advertisement data of at least one product of the service providing company.

As another embodiment, the payment calculation unit 224 may differentially calculate the amount of money to be paid to the user according to at least one of user information items that have been agreed in advance to externally provide, the user's frequency of using the massage equipment, and the accumulated amount of money that the user has paid for at least one product of the service providing company.

To this end, the product use management unit 223 may cumulatively calculate the amount of money that the user has paid for at least one product of the service providing company. For this purpose, every time the user pays for a product of the service providing company, details of spending may be mapped to the user account and stored in the database unit 230.

Then, the payment calculation unit 224 may differentially calculate the amount of money to be paid to the user according to the cumulatively calculated amount of money.

For example, the payment calculation unit 224 may increase the calculated amount of money when the cumulatively calculated amount of money that the user has paid for at least one product of the service providing company increases. To this end, it is possible to use a weight table which is differentially set according to the cumulative amount of money that the user has paid, and the weight table may be updated by the service providing server 200.

Here, the final amount of money calculated by the payment calculation unit 224 may be calculated in consideration of the number and types of user information items that have been agreed in advance to externally provide, the user's frequency of using the massage equipment, and the cumulative amount of money that the user has paid for at least one product of the service providing company.

As still another embodiment, the payment calculation unit 224 may differentially calculate the amount of money to be paid to the user according to at least one of user information items that have been agreed in advance to externally provide, the user's frequency of using the massage equipment, and current rental status information of at least one product of the service providing company.

To this end, every time the user makes a contract for a product rental service, the service company server 200 may map rental information to the user account and store the rental information in the database unit 230.

The payment calculation unit 224 may calculate a remaining time period from the current time point to a time point at which the product rental ends and determine whether the remaining time period until the time point at which the product rental ends corresponds to a preset promotion time period. Also, the payment calculation unit 224 may differentially calculate the amount of money to be paid to the user according to whether the remaining time period until the time point at which the product rental ends corresponds to the preset promotion time period.

For example, when the remaining time period until the time point at which the product rental ends corresponds to the preset promotion time period, the payment calculation unit 224 may set the calculated amount of money to be paid to the user to be greater than that of a case in which the remaining time period does not correspond to the preset promotion time period. In this way, the user may use the paid money to extend the rental period or purchase another product, and also the paid money is accumulated so that the user may be motivated to purchase a product.

Here, the final amount of money calculated by the payment calculation unit 224 may be calculated in consideration of the number and types of user information items that have been agreed in advance to externally provide, the user's frequency of using the massage equipment, and the user's current rental status of at least one product of the service providing company.

The dedicated virtual currency administration unit 224 may use blockchain-based dedicated virtual currency when a selling and buying transaction occurs among the user, the service providing company, and a third party company.

Specifically, in the case of selling user information provided by the user to the third party company, the dedicated virtual currency administration unit 224 may calculate the amount of money to be paid in return to the user who has provided the user information in the dedicated virtual currency. Also, the dedicated virtual currency administration unit 225 may give the calculated dedicated virtual currency to the user account. The user account may be, for example, an electronic purse. The user may use the dedicated virtual currency to purchase or rent another product of the service providing company or to use a paid service.

Figure 4:
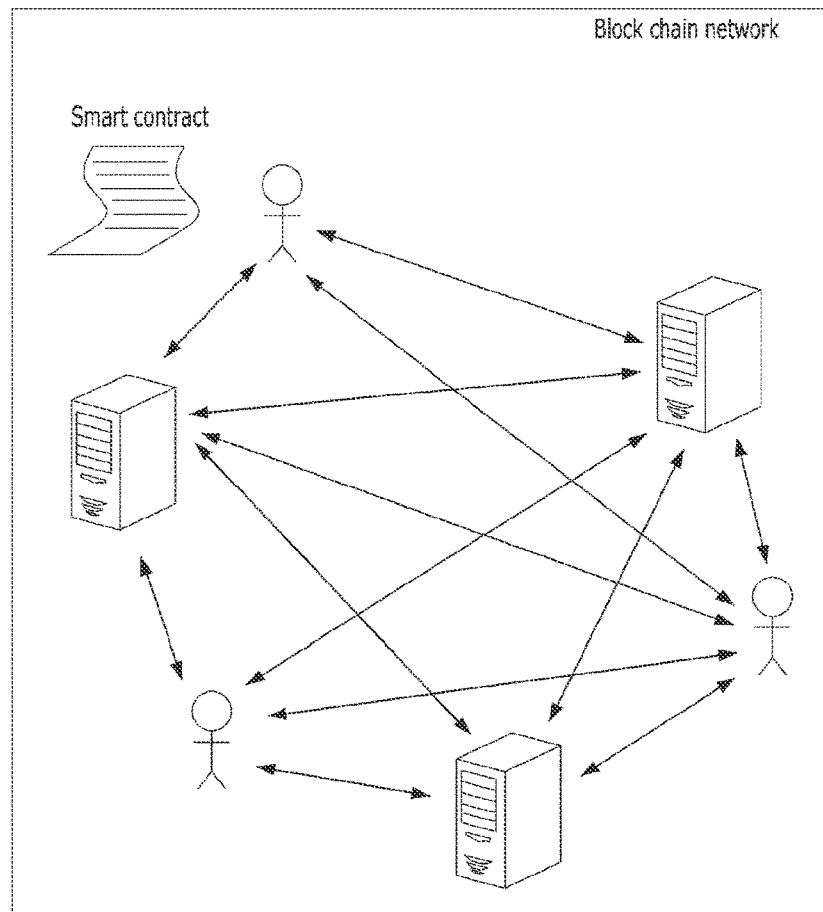
FIG. 4 is a diagram schematically showing a blockchain-based user information transaction system according to an embodiment of the present disclosure.
Figure 5:
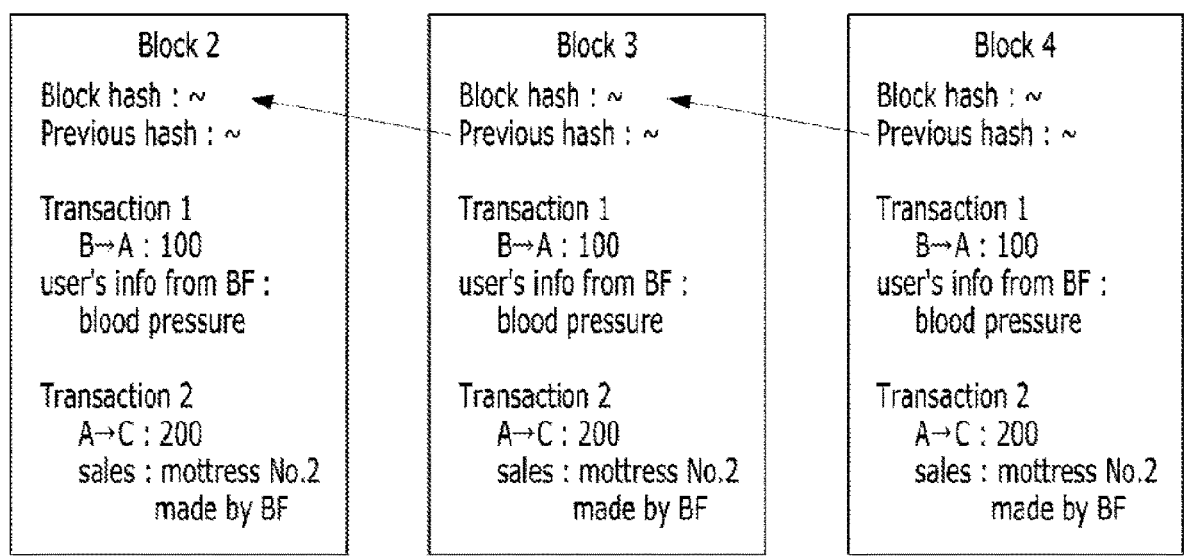
FIG. 5 is a set of diagrams schematically showing an example of a blockchain according to an embodiment of the present disclosure.

FIG. 4 is a diagram schematically showing a blockchain-based user information transaction system according to an embodiment of the present disclosure, and FIG. 5 is a set of diagrams schematically showing an example of a blockchain according to an embodiment of the present disclosure.

As shown in FIG. 4, the dedicated virtual currency administration unit 224 may use dedicated virtual currency based on a smart contract which is set to automatically transfer the dedicated virtual currency to a corresponding target when a specific condition is satisfied in a blockchain network.

The smart contract may be set to generate a transaction which includes transfer path and detailed usage information of corresponding user information together with details of a dedicated cryptocurrency transaction.

In other words, a smart contract used in the present disclosure may be set as shown in FIG. 5 so that a transfer path of user information and details of selling and buying user information may be stored in a blockchain when a dedicated virtual currency transaction occurs for a user information transaction. In this case, among pieces of information stored in the blockchain, personal information, such as personal identity information and unique identification information, may be encrypted. In other words, only information related to a transfer path of the user information and details of user information usage may be stored, and the security of sensitive personal information may be maintained through encryption.

All nodes constituting the blockchain network participate in blockchain distributed consensus, and thus all the nodes share the same transaction.

Accordingly, in practice, no one can forge and leak details of selling and buying user information. Consequently, it is possible to ensure transaction integrity, prevent manipulation of transaction details, and prevent a double spending attack.

Also, since the dedicated virtual currency administration unit 245 transacts user information on the basis of the blockchain, a corresponding user may be rewarded every time corresponding user information is sold to a third party company.

The user may use the rewarded dedicated virtual currency to pay the seller of the massage equipment 1000 for a rent or follow-up service, to purchase a small massage device, cosmetics, and health functional food, to upgrade a sound source and program, and the like. Also, the user may use the rewarded dedicated virtual currency in other companies, hospitals, insurance companies, etc. which are contracted to handle the dedicated virtual currency. Further, the user may withdraw the dedicated virtual currency or exchange the virtual currency to Korean won at a trading center which handles the dedicated virtual currency.

Figure 6:
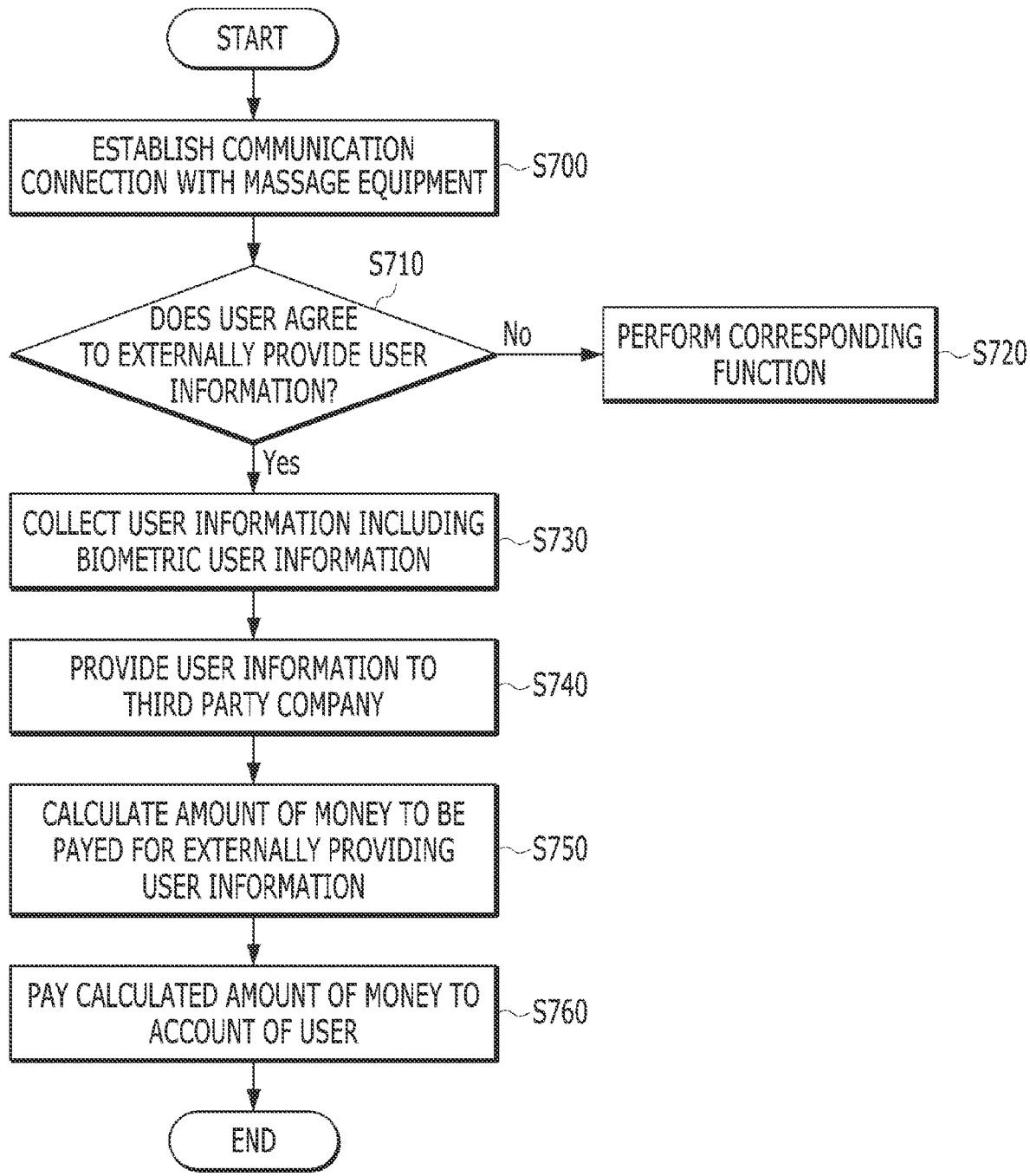
FIG. 6 is a flowchart illustrating a method of transacting user information on the basis of massage equipment according to an embodiment of the present disclosure.

FIG. 6 is a flowchart illustrating a method of transacting user information on the basis of massage equipment according to an embodiment of the present disclosure. Roles of and relationships between elements for user information transaction based on massage equipment have been described above with reference to FIGS. 1 to 5.

Referring to FIG. 6, in the method of transacting user information on the basis of massage equipment according to the embodiment of the present disclosure, the service providing server 200 may first establish a communication connection with the massage equipment 1000 (S700).

Here, the massage equipment 1000 may include the at least one biometric information measurement module 4000. The biometric information measurement module 4000 may be installed in the massage equipment 1000 or provided outside the massage equipment 1000 and may be connected to the massage equipment control device 2000 through wired or wireless communication. A biometric measurement signal measured by the biometric information measurement module 4000 may be transmitted to the massage equipment control device 2000.

The biometric information measurement module 4000 may include at least one of a sphygmomanometer, a blood glucose meter, a hematology analyzer, an electrocardiograph recorder, an electroencephalogram device, a body-composition measurement device, an electronic stethoscope, a peak flow meter, a momentum meter, a weighing machine, a body fat analyzer, medical image equipment, and a urinalysis machine. As a means for acquiring a user's life-log data and information related to lifestyle medicine, the biometric information measurement module 4000 may further include an electronic device and the like which interoperates with the massage equipment 1000.

An application programmed for the purpose of acquiring information required by the massage equipment 1000 may run on the electronic device. Such an electronic device may directly receive information from users or collect genomic information, medical information, and physical information of the users in conjunction with a system of a medical institution, such as a hospital, a third party company, and the like. Here, the information related to lifestyle medicine may include information on an amount of exercise, intakes, drinking, smoking, defecation, sleep, and the like.

The massage equipment 1000 may build a database from time-series health information of each individual on the basis of at least one of biometric information, life-log data, information related to lifestyle medicine, user genome information, medical treatment information, electronic medical records, and physical information.

Also, the massage equipment 1000 may not handle user information in the form of simple information and may process collected information as customized information through a specific algorithm. The specific algorithm may be, for example, early myocardial infarction and heart attack diagnosis algorithm, an early cerebral infarction diagnosis algorithm, an early dementia diagnosis algorithm, an early obesity diagnosis algorithm, and diagnosis and prevention algorithms for various types of other diseases.

The massage equipment 1000 may provide information in a connective and integrated form in consideration of a lifestyle closely related to a biometric signal or relationships between a plurality of biometric signals which are related to each other.

As an embodiment, the massage equipment 1000 may match blood pressure value information obtained by measuring a blood pressure to life-log data which affects the blood pressure and information related to lifestyle medicine and process the result as a dataset.

Such a dataset according to the embodiment of the present disclosure may be constantly generated through the massage equipment every day. Since the dataset is not simply generated from biometric value information but is generated by matching the biometric value information to genomic information which affects biometric values, past medical record information, life-log data, and information related to lifestyle medicine, the dataset has a utility value as medical user data, and it is possible to increase the accuracy and reliability of data. Also, users can easily acquire various types of information while using the massage equipment 1000 without visiting a hospital or an expert organization.

Further, the massage equipment 1000 may additionally generate and provide information for predicting a future health condition on the basis of such a database. As an embodiment, the massage equipment 1000 may analyze at least one of daily measured electrocardiogram values, daily measured blood cholesterol values, daily measured blood pressure values, the number of times, intensity, and duration of exercise during a predetermined time period, the number of drinking times and the volume of drink during a predetermined time period, sleeping hours, the number of smoking times, and the amount of smoking and calculate symptomatic information of various diseases, such as a probability of the user developing a cardiovascular disease in the future, and development prediction information of a corresponding symptom.

To this end, the massage equipment 1000 may access a statistical information database which stores various types biometric information, life-log data, information related to lifestyle medicine, user genome information, statistical information experientially or numerically calculated from medical treatment information, electronic medical records, and a time period from when a symptom of a disease related to physical information appears to when the disease develops, and disease-specific symptomatic information related to types and symptoms of various diseases.

Also, the massage equipment 1000 according to the embodiment of the present disclosure may provide a customized massage according to user information acquired in the above-described manner. The customized massage may include a blood pressure control massage, a dementia prevention massage, a depression prevention massage, and a massage for preventing a specific disorder.

Subsequently, the service providing server 200 may inquire of the user whether the user agrees to externally provide user information in advance (S710).

For example, the service providing server 200 may inquire whether the user agrees in advance through an execution screen of a display or voice from a speaker and receive an answer to the inquiry from the user.

When the user input advance consent to externally provide user information in advance, the massage equipment control device 2000 may further provide a screen for selecting a predetermined item that will be agreed to externally provide in advance from among one or more biometric user information items according to the user's request.

Alternatively, the massage equipment control device 2000 may provide an execution screen for selecting at least one biometric user information item from the beginning and also provide an execution screen which has been set to agree in advance to externally provide biometric user information only corresponding to the selected item.

For example, the user may selectively check only items corresponding to physical information that he or she wants to provide regarding at least one biometric information item among blood pressure, blood glucose, blood test, electronic stethoscope examination, expiratory flow, the amount of exercise, weight, body fat, medical image, and frequent urination.

Here, the massage equipment control device 2000 may selectively turn on or off a biometric information measurement module corresponding to the item selected by the user. For example, the massage equipment control device 2000 may automatically turn on only the biometric information measurement module corresponding to the item selected by the user to acquire a biometric measurement signal of the user and may automatically turn off the biometric information measurement module when the acquired biometric measurement signal is stored in the massage equipment control device 2000. In this way, it is unnecessary to turn on the power of all biometric information measurement modules provided in the massage equipment, and it is possible to efficiently manage power consumed by the massage equipment by only turning on a necessary biometric information measurement module.

Alternatively, the massage equipment control device 2000 may only collect a biometric measurement signal corresponding to an item that has been agreed in advance by the user among biometric measurement signals acquired from a plurality of biometric information measurement modules.

When there is an item that has been agreed in advance by the user to externally provide user information, the massage equipment control device 2000 may perform user authentication. For example, the massage equipment control device 2000 may provide a user authentication screen. When the user inputs an ID and a password to the user authentication screen, the service providing server 200 performs user authentication by checking whether the input ID and password coincide with an ID and password previously stored in a database.

Subsequently, when the user agrees in advance to the inquiry about whether the user agrees to externally provide user information, the service providing server 200 may collect and store user information including biometric user information from the massage equipment (S730).

In other words, after the user authentication succeeds, the service providing server 200 maps a unique identifier of the authenticated user to a biometric measurement signal acquired from the biometric information measurement module 4000 and store the result as user information. Here, the user information may mean information obtained by mapping the user's individual identification information to the biometric measurement signal (hereinafter, a biometric measurement signal and biometric information may be interchangeably used).

The service providing server 200 maps the biometric user information to the user identification information and stores the biometric user information and the user identification information. This is a necessary process to pay the user for providing the user information and may also be a process required for the purpose of recognizing a change in the biometric measurement signal of the user over time and the like.

At a time point at which user information is sold to the third party company server 300 by the service providing server 200, personal identity information, unique identification information, etc. may be excluded from the user information or encrypted. In other words, the user information may be provided so that only information related to biometric measurement signals required by the third party company may be provided, and the security of sensitive personal information may be maintained. Here, the third party company may be at least one of a medical institution, an insurance company, a pharmaceutical company, a health food company, and a data exchange. The third party company may use information on the user, which is constant, connective, and integrated information acquired through the service providing server 200, in various businesses. For example, the third party company may use a plurality of pieces of user information in businesses such as generating health functional food, planning a customized exercise, proposing a customized diet, generating a diet program, and generating a program for preventing a specific disease.

The service providing server 200 may perform the above-described functions through a dedicated application. For example, the dedicated application may be downloaded from the service providing server 200 to the massage equipment control device 2000 through a network and installed.

Alternatively, when the massage equipment control device 2000 is a dedicated smart device of the massage equipment 1000 or a built-in module included in the massage equipment 1000, the dedicated application may be installed on the massage equipment control device 2000 by default during product manufacturing or production.

Each of a plurality of massage equipment 1000 may transmit user information acquired from each user to the service providing server 200. Also, one massage equipment 1000 may transmit pieces of user information separately acquired from a plurality of users to the service providing server 2000.

Subsequently, the service providing server 200 may provide the stored user information to a third party company server (S740).

In other words, the service providing server 200 may transact the user information with a third party company server. In this case, among the pieces of user information, only biometric information may be provided, and sensitive personal information, such as personal identity information and unique personal identification information, may be excluded or encrypted and provided.

Subsequently, the service providing server 200 may calculate the amount of money to be paid to the user for externally providing the user information (S750).

In other words, the service providing server 200 may calculate the amount of money to be paid to the user according to a price at which the service providing company sells the user information to the third party company.

Specifically, when calculating the amount of money to be paid to the user, the service providing server 200 may differentially calculate the amount of money according to user information items that have been agreed in advance to externally provide and the user's frequency of using the massage equipment and pay the user the amount of money.

To this end, first, the service providing server 200 may acquire at least one of the number of user information items that have been agreed in advance to externally provide and types of the items. Also, the service providing server 200 may acquire the user's frequency of using the massage equipment 1000. Here, the user's frequency of using the massage equipment 1000 may be the number of times of use during a preset certain time period. The number of user information items that have been agreed in advance to externally provide, types of the items, and the user's frequency of using the massage equipment 1000 may be acquired from the database unit 230. Subsequently, the service providing server 200 may calculate the amount of money to be paid to the user in consideration of at least one of the number of user information items that have been agreed in advance to externally provide, types of the items, and the user's frequency of using the massage equipment 1000.

For example, when the user selects the items of blood pressure, weight, and body fat as user information, it is possible to calculate a part of the amount of money to be paid to the user by applying a weight which is differentially set according to the importance of each item and the number of selected items. Also, it is possible to calculate a part of the amount of money to be paid to the user by applying a weight which is differentially set according to the user's frequency of using the massage equipment 1000 during a preset time period. The total amount of money to be paid to the user may be calculated in consideration of the two amounts of dedicated virtual currency calculated as described above. The weights may be acquired from the database unit 230 and updated by the service providing server 200.

In the case of calculating the amount of money to be paid, the frequency of using the massage equipment 1000 is taken into consideration to motivate the user to continuously use the massage equipment 1000 so that the user may fully use the performance of the massage equipment 1000 and obtain positive massage effects on his or her body.

Also, the service providing server 200 may calculate the amount of money as a compensation for a user who has used the massage equipment 1000 for a predetermined time or more and a predetermined number of times or more during a predetermined time period.

In addition, the service providing server 200 may additionally pay for a specific event, which may be, for example, a case in which a user with a specific disease constantly provides user information in time series or a case in which a user acquires and provides genomic information and the like from a medical institution or a corresponding expert organization.

When calculating the amount of money to be paid to the user, the service providing server 200 may differentially calculate the amount of money according to at least one of the user information items that have been agreed in advance to externally provide, the user's frequency of using the massage equipment and pay the user the amount of money, and the user's detailed usage information related to various types of products of the company. Specific embodiments of calculating the amount of money to be paid to the user on the basis of such information will be described.

As an embodiment, the service providing server 200 may differentially calculate the amount of money to be paid to the user according to at least one of user information items that have been agreed in advance to externally provide, the user's frequency of using the massage equipment, and a current situation of uploading advertisement data of at least one product of the service providing company.

To this end, the service providing server 200 may calculate the number of times that the user has uploaded advertising content of at least one product of the service providing company online. Here, information on the number of times of uploading advertising content may be updated in real time in the database unit 230 through the dedicated application.

Also, the service providing server 200 may acquire priority order information preset by the service providing company for the product of which the advertising content has been uploaded. Subsequently, the service providing server 200 may calculate the amount of money to be paid in consideration of the number of times of uploading the advertising content and the acquired priority order information.

For example, the service providing company is a company related to healthcare products and sells massage equipment, water purifiers, air purifiers, mattresses or provides a rental service thereof. Among the products, the service providing company focuses on massage equipment as a representative product, and thus the highest order of importance may be given to the massage equipment among the products. Also, the service providing company may separately determine orders of importance for several types of massage equipment according to the functions, unit prices, etc. thereof. Information on the set order of importance may be stored in the database unit 230 and updated by the service providing server 200. Information on the number of times of uploading advertising content may be stored in the database unit 230 as the number of times that the advertising content has been uploaded to SNSs during a predetermined time period and may be updated by the service providing server 200.

The service providing server 200 may increase the calculated amount of money when the user purchases a type of massage equipment with a higher order of importance among types of massage equipment and shares advertising content through SNSs a greater number of times during a predetermined time period. To this end, it is possible to use a weight table of weights which are differentially set according to the order of importance of products, weights which are differentially set according to the number of times of uploading advertising content during a predetermined time period, etc., and the weight table may be updated by the service providing server 200.

Here, the final amount of money calculated by the service providing server 200 may be calculated in consideration of the number and types of user information items that have been agreed in advance to externally provide, the user's frequency of using the massage equipment, and a current situation of uploading advertisement data of at least one product of the service providing company.

As another embodiment, the service providing server 200 may differentially calculate the amount of money to be paid to the user according to at least one of user information items that have been agreed in advance to externally provide, the user's frequency of using the massage equipment, and the accumulated amount of money that the user has paid for at least one product of the service providing company.

To this end, the service providing server 200 may cumulatively calculate the amount of money that the user has paid for at least one product of the service providing company. For this purpose, every time the user pays for a product of the service providing company, details of spending may be mapped to the user account and stored in the database unit 230.

Then, the service providing server 200 may differentially calculate the amount of money to be paid to the user according to the cumulatively calculated amount of money.

For example, the service providing server 200 may increase the calculated amount of money when the cumulatively calculated amount of money that the user has paid for at least one product of the service providing company increases. To this end, it is possible to use a weight table which is differentially set according to the cumulative amount of money that the user has paid, and the weight table may be updated by the service providing server 200.

Here, the final amount of money calculated by the service providing server 200 may be calculated in consideration of the number and types of user information items that have been agreed in advance to externally provide, the user's frequency of using the massage equipment, and the cumulative amount of money that the user has paid for at least one product of the service providing company.

As still another embodiment, the service providing server 200 may differentially calculate the amount of money to be paid to the user according to at least one of user information items that have been agreed in advance to externally provide, the user's frequency of using the massage equipment, and a current rental status of at least one product of the service providing company.

To this end, every time the user makes a contract for a product rental service, the service company server 200 may map rental information to the user account and store the rental information in the database unit 230.

The service providing server 200 may calculate a remaining time period from the current time point to a time point at which the product rental ends and determine whether the remaining time period until the time point at which the product rental ends corresponds to a preset promotion time period. Also, the service providing server 200 may differentially calculate the amount of money to be paid to the user according to whether the remaining time period until the time point at which the product rental ends corresponds to the preset promotion time period.

For example, when the remaining time period until the time point at which the product rental ends corresponds to the preset promotion time period, the service providing server 200 may set the calculated amount of money to be paid to the user to be greater than that of a case in which the remaining time period does not correspond to the preset promotion time period. In this way, the user may use the paid money to extend the rental period or purchase another product, and also the paid money is accumulated so that the user may be motivated to purchase a product.

Here, the final amount of money calculated by the service providing server 200 may be calculated in consideration of the number and types of user information items that have been agreed in advance to externally provide, the user's frequency of using the massage equipment, and the user's current rental status of at least one product of the service providing company.

Subsequently, the service providing server 200 may pay the calculated amount of money to the account of the user (S760).

In this case, when selling the user information provided by the user to the third party company, the service providing server 200 may calculate, in the dedicated virtual currency, the amount of money to be paid to the user for providing the user information. Also, the service providing server 200 may give the calculated dedicated virtual currency to the user account. The user account may be, for example, an electronic purse. The user may use the dedicated virtual currency to purchase or rent another product of the service providing company or to use a paid service.

It is possible to use dedicated virtual currency based on a smart contract which is set to automatically transfer the dedicated virtual currency to a corresponding target when a specific condition is satisfied in a blockchain network.

The smart contract may be set to generate a transaction which includes transfer path and detailed usage information of corresponding user information together with details of a dedicated cryptocurrency transaction.

In other words, a smart contract used in the present disclosure may be set so that a transfer path of user information and details of selling and buying user information may be stored in a blockchain when a dedicated virtual currency transaction occurs. In this case, among pieces of information stored in the blockchain, personal information, such as personal identity information and unique identification information, may be excluded or encrypted. In other words, only information related to a transfer path of the user information and details of user information usage may be stored, and the security of sensitive personal information may be maintained through encryption.

All nodes constituting the blockchain network participate in blockchain distributed consensus, and thus all the nodes share the same transaction.

Accordingly, in practice, no one can forge and leak details of selling and buying user information. Consequently, it is possible to ensure transaction integrity, prevent manipulation of transaction details, and prevent a double spending attack.

Also, since the service providing server 200 transacts user information on the basis of the blockchain, a corresponding user may be rewarded every time user information is sold to a third party company.

With the massage equipment-based user information transaction method and system configured as described above according to the embodiments of the present disclosure, a user can immediately acquire his or her own biometric information while using massage equipment and can be rewarded for externally providing his or her own acquired biometric information.

Also, when rewarding a user for selling user information, a company differentially pays the amount of money by applying a weight according to details of using a variety of products thereof including the frequency of using massage equipment. Accordingly, it is possible to increase sales in the end by motivating the user to consume products of the company.

Further, when blockchain-based dedicated virtual currency is used in buying and selling transactions among a massage equipment user, a service company, and a third party company, it is possible to track a transfer path of user information and detailed usage information of the user information, and details of buying and selling transactions cannot be forged. Accordingly, it is possible to realize a reliable selling and buying transaction system.

The user may use the rewarded dedicated virtual currency to pay the seller of the massage equipment 1000 for a rent or follow-up service, to purchase a small massage device, cosmetics, and health functional food, to upgrade a sound source and program, and the like. Also, the user may use the rewarded dedicated virtual currency in other companies, hospitals, insurance companies, etc. which are contracted to handle the dedicated virtual currency. Further, the user may withdraw the dedicated virtual currency or exchange the virtual currency to Korean won at a trading center which handles the virtual currency.

Those of ordinary skill in the art to which the present invention pertains should appreciate that the present invention can be implemented in cooperation with other program modules and/or as a combination of hardware and software. For example, the present invention can be implemented by a computer-readable medium.

Any medium that can be accessed by a computer may be the computer-readable medium, and the computer-readable medium includes volatile and non-volatile media, transitory and non-transitory media, and removable and non-removable media. As a non-limited example, the computer-readable medium may include a computer-readable storage medium and a computer-readable transmission medium.

The computer-readable storage medium includes volatile and non-volatile media, transitory and non-transitory media, and removable and non-removable media which are implemented by an arbitrary method or technology for storing information such as a computer-readable command, a data structure, a program module, or other data. The computer-readable storage medium includes a random access memory (RAM), a read only memory (ROM), an electrically erasable and programmable read only memory (EEPROM), a flash memory, other memory technologies, a compact disk read only memory (CD-ROM), a digital video disk (DVD), other optical disk storage devices, a magnetic cassette, a magnetic tape, a magnetic disk storage device, other magnetic storage device, or other media which can be accessed by a computer and used to store desired information, but the computer-readable storage medium is not limited thereto.

The computer-readable transmission medium generally implements a computer-readable command, a data structure, a program module, other data, or the like in a modulated data signal, such as a transport mechanism, and includes all information transmission media. The term "modulated data signal" means a signal of which one or more characteristics are set or changed to encode information in the signal. As a non-limited example, the computer-readable transmission medium includes a wired medium, such as a wired network or a direct-wired connection, and a wireless medium, such as a sound, a radio frequency (RF), infrared rays, or other wireless media. A combination of some of the aforementioned media is also included in the computer-readable transmission medium.

Those of ordinary skill in the art may understand that various exemplary logical blocks, modules, processors, means, circuits, and algorithm steps described in relation to the embodiments disclosed herein may be implemented by electronic hardware, various types of program or design codes (for convenience, referred to as "software" herein), or a combination thereof. To clearly describe inter-compatibility of hardware and software, various exemplary components, blocks, modules, circuits, and steps have been generally described above in relation to the functions thereof. Whether the function is implemented as hardware or software depends on design limitations imposed on a specific application and the entire system. Those of ordinary skill in the art may implement the described functions with various methods for each specific application, but a determination of the implementation should not be construed as departing from the scope of the present invention.

Various embodiments proposed herein may be implemented as a manufactured article using a method, an apparatus, standard programming, and/or an engineering technology. The term "manufactured article" includes a computer program, a carrier, or media that can be accessed by an arbitrary computer-readable device. For example, the computer-readable storage medium includes a magnetic storage device (e.g., a hard disk, a floppy disk, and a magnetic strip), an optical disk (e.g., a CD and a DVD), a smart card, and a flash memory (e.g., an EEPROM, a card, a stick, and a key drive) but is not limited thereto. The term "machine-readable medium" includes a wireless channel and other various media capable of storing, holding, and/or transmitting a command and/or data but is not limited thereto.

It should be understood that a specific sequence or hierarchy structure of steps in the proposed processes is an example of exemplary approaches. It should be understood that, on the basis of a design priority, a specific sequence or a hierarchy structure of steps in the proposed processes may be rearranged within the scope of the present invention. The accompanying method claims provide elements of various steps in a sample sequence but do not mean limitation to the specific sequence or hierarchy structure.

Description of the proposed embodiments is provided so that those of ordinary skill in the art may use or carry out the present invention. Various modifications of the embodiments may be apparent to those of ordinary skill in the art, and general principles defined herein may be applied to other embodiments without departing from the scope of the present invention. Accordingly, the present invention is not limited to the embodiments proposed herein and should be interpreted within the broadest range of meaning consistent with the principles and new characteristics proposed herein.

The invention claimed is:

1. A method of managing user information with massage equipment having a body massage assembly, a leg massage assembly, and a biometric information measurement sensor, wherein the massage equipment is configured to communicate with a massage equipment control device through wired or wireless communication, the method comprising:
   collecting and storing, via the massage equipment control device, the user information, wherein the user information comprises at least one of:
      biometric information of a user obtained from the biometric information measurement sensor and
      personal information of the user obtained from the user or information providers;
   transmitting, via the massage equipment control device, the user information to a service-providing server storing a medical algorithm for diagnosing disease;
   receiving, by the massage equipment, a result of an analysis of the user information by the medical algorithm from the service-providing server;
   providing a customized massage, by the massage equipment, to prevent or treat the disease in response to the result of the analysis by the medical algorithm; and providing the user information, via the service-providing server, to a third-party company server, wherein the service-providing server calculates an amount of reward to the user, based on a weighted value for externally providing the user information, and pays the amount of reward to the user to an account of the user.

2. The method of claim 1, wherein the collecting and storing of the user information comprises:

measuring biometric information through the biometric information measurement sensor provided in the massage equipment, wherein the biometric information measurement sensor is at least one of a blood glucose meter, a hematology analyzer, an electrocardiograph recorder, a body-composition measurement device, a peak flow meter, a momentum meter, a weighing machine, medical image equipment, and a urinalysis machine;

acquiring at least one of the user's life-log data, information related to lifestyle medicine, genome information, and medical treatment information through an electronic device interoperating with the massage equipment; and building a database from time-series health information of each user using at least one of the biometric information, the life-log data, the information related to lifestyle medicine, the genome information, and the medical treatment information.

3. The method of claim 2, wherein the providing the user information to the third-party company server further comprises:

acquiring data by selecting at least one of:
a user's detailed usage information,
a user's frequency of using the massage equipment, and
a number of categories of the biometric information collected through a user selection;

setting the
weighted value differentially according to the data and weight table information; and
calculating the amount of reward to the user by applying the weighted value.

4. The method of claim 3, wherein the acquiring of the user's detailed usage information comprises:

calculating a number of times that the user has uploaded advertising content of at least one product of a company online; and acquiring priority order information preset by the company for the product of which the advertising content has been uploaded.

5. The method of claim 3, wherein the acquiring the user's detailed usage information comprises cumulatively calculating the amount of reward that the user has paid for at least one product of a company.

6. The method of claim 3, wherein the acquiring of the user's detailed usage information comprises:

acquiring the user's current rental status information of at least one product of a company;

calculating a time period remaining until a time point at which rental ends from the current rental status information; and determining whether the time period remaining until the time point at which the rental ends corresponds to a preset promotion time period.

7. The method of claim 1, wherein the paying the amount of reward to the user to the account of the user comprises paying the amount of reward in a dedicated virtual currency through a blockchain, and when the dedicated virtual currency is paid, the blockchain includes details of a transfer path of the user information.

8. A system for managing user information, the system comprising massage equipment, which has a body massage assembly; a leg massage assembly; and a biometric information measurement sensor, wherein the massage equipment is configured to communicate with a massage equipment control device through wired or wireless communication, and wherein the massage equipment is configured to:
collect and store, via the massage equipment control device, the user information, wherein the user information comprises at least one of:
biometric information of a user obtained from the biometric information measurement sensor and
personal information of the user obtained from the user or information providers;

transmit, via the massage equipment control device, the user information to a service-providing server storing a medical algorithm for diagnosing disease;

receive, by the massage equipment, a result of an analysis of the user information by the medical algorithm from the service-providing server;

provide a customized massage, by the massage equipment, to prevent or treat the disease in response to the result of the analysis by the medical algorithm; and provide the user information, via the service-providing server, to a third-party company server, wherein the service-providing server calculates an amount of reward to the user, based on a weighted value for externally providing the user information, and pays the amount of reward to the user to an account of the user.

9. The system of claim 8, wherein the service providing server acquires data by selecting at least one of:
a user's detailed usage information,
a user's frequency of using the massage equipment, and
a number of categories of the biometric information collected through a user selection;
and calculates the amount of reward to be paid to the user.

10. The system of claim 9, wherein the service providing server acquires of the user's detailed usage information by calculating a number of times that the user has uploaded advertising content of at least one product of a company online; and acquiring priority order information preset by the company for the product of which the advertising content has been uploaded.

11. The system of claim 9, wherein the service providing server cumulatively calculates, as the user's detailed usage information, the amount of reward that the user has paid for at least one product of a company.

12. The system of claim 9, wherein the service providing server acquires, as the user's detailed usage information, the user's current rental status information of at least one product of a company, calculates a time period remaining until a time point at which rental ends from the current rental status information, and determines whether the time period remaining until the time point at which the rental ends corresponds to a preset promotion time period.

13. The system of claim 9, wherein the service providing server pays the amount of reward to the user account in a dedicated virtual currency through a blockchain, and the blockchain includes details of a transfer path of the user information.

14. The method of claim 1, wherein the analyzing, by the medical algorithm on the massage equipment, the user information for diagnosing disease comprises:
building a database from time-series health information for each user on the basis of at least one of biometric information, life-log data, lifestyle medicine information, user genome information, medical treatment information, electronic medical records, and physical information,
processing the user information, by the medical algorithm, to make customized information, wherein the medical algorithm includes at least one of early myocardial infarction and heart attack diagnosis algorithm and early obesity diagnosis algorithm.

15. The method of claim 14, wherein the massage equipment is configured to measure and match blood pressure value information to the life-log data and processes a result thereof as the dataset.

16. The method of claim 1, wherein the customized massage comprises at least one of a blood pressure control massage, a dementia prevention massage, and a depression prevention massage.

17. The system of claim 8, wherein the analyzing, by the medical algorithm on the massage equipment, the user information for diagnosing disease comprises:
building a database from time-series health information for each user on the basis of at least one of biometric information, life-log data, lifestyle medicine information, user genome information, medical treatment information, electronic medical records, and physical information,
processing the user information, by the medical algorithm, to make customized information, wherein the medical algorithm includes at least one of early myocardial infarction and heart attack diagnosis algorithm and early obesity diagnosis algorithm.

18. The system of claim 17, wherein the massage equipment is configured to measure and match blood pressure value information to the life-log data and processes a result thereof as the dataset.

19. The system of claim 8, wherein the customized massage comprises at least one of a blood pressure control massage, a dementia prevention massage, and a depression prevention massage.

\* \* \* \* \*